United States Patent [19]
Facchini

[11] Patent Number: 6,147,070
[45] Date of Patent: Nov. 14, 2000

[54] METHODS AND COMPOSITIONS FOR CONTROLLING IRON STORES TO TREAT AND CURE DISEASE STATES

[76] Inventor: Francesco Facchini, 2145 California St., #1, San Francisco, Calif. 94115

[21] Appl. No.: 09/092,521

[22] Filed: Jun. 5, 1998

[51] Int. Cl.$^7$ .................................................. A01N 55/04
[52] U.S. Cl. ........................ 514/189; 514/185; 424/675; 424/678; 424/686
[58] Field of Search .................................. 514/185, 189; 424/675, 678, 686

[56] References Cited

U.S. PATENT DOCUMENTS

| | | | |
|---|---|---|---|
| 4,952,568 | 8/1990 | Sawai et al. ............................. | 514/103 |
| 5,162,313 | 11/1992 | Kappas et al. .......................... | 514/183 |
| 5,190,970 | 3/1993 | Pan et al. ................................ | 514/423 |
| 5,223,494 | 6/1993 | Kappas et al. .......................... | 514/185 |
| 5,298,525 | 3/1994 | Yoon et al. .............................. | 514/460 |
| 5,762,936 | 6/1998 | Ronzio et al. ........................ | 424/195.1 |
| 5,990,153 | 11/1999 | Wood et al. ............................ | 514/440 |

OTHER PUBLICATIONS

Cutler, P., "Deferoxamine Therapy in High–Ferritin Diabetes," Diabetes, vol. 38, Oct. 1989, pp. 1207–1210.
Weintraub et al., "The Treatment of Hemochromatosis by Phlebotomy", Med. Clin. North Am., vol. 50, No. 6, 1966, pp. 1579–1590.
Cecil Textbook of Medicine, 19th edition, W.B. Saunders Co., p. 1135, 1993.
Remington: The Science and Practice of Pharmacy, 19th edition, Mack Publishing Co., Chapter 54, p. 934, 1995.
Balla, G., et al. "Hemin: A Possible Physiological Mediator of Low Density Lipoprotein Oxidation and Endothelial Injury," Arteriosclerosis and Thrombosis, vol. 11, No. 6, Nov./Dec. 1991, pp. 1700–1711.
Bennett, P.H., et al., "Definition, Diagnosis, and Classification of Diabetes Mellitus and Impaired Glucose Tolerance," Chapter 11, Joslin's Diabetes Mellitus, 13th Edition, 1994, pp. 193–200.
Blake, D.R., et al., "Cerebral and Ocular Toxicity Induced by Desferrioxamine," Quarterly Journal of Medicine, New Series 56, No. 219, Jul. 1985, pp. 345–355.
Boni, R.E., et al. "Tin–Mesoporphyrin Inhibits Heme Oxygenase Activity and Heme–Iron Absorption in the Intestine," Pharmacology, vol. 47, 1993, pp. 318–329.
Comiancini, L., et al., "Troglitazone Reduces LDL Oxidation and Lowers Plasma E–selectin Concentration in NIDDM Patients," Diabetes, vol. 17, Jan. 1998, pp. 130–133.
Dymock, I.W., "Observations on the Pathogenesis, Complications and Treatment of Diabetes in 115 Cases of Haemochromatosis," The American Journal of Medicine, vol. 52, Feb. 1972, pp. 203–209.
Facchini, F., et al., "Light–to–Moderate Alcohol Intake is Associated With Enhanced Insulin Sensitivity," Diabetes Care, vol. 17, No. 2, Feb. 1994, pp. 115–119.

(List continued on next page.)

Primary Examiner—Dwayne C. Jones
Attorney, Agent, or Firm—Fish & Neave; Nicola A. Pisano

[57] ABSTRACT

Methods and compositions of matter are provided that enable a phased reduction of body iron stores to near a iron deficiency level, and thereafter maintain the body iron stores at that level by reducing further iron accumulation. In a first phase, a patient's body iron stores are reduced to a level of near iron deficiency by regular periodic phlebotomy or use of pharmacological agents, such as iron chelators, for example, over a period of six to twelve months. In a second phase, ingested iron absorption is controlled using an oral dose, taken at mealtimes, of compound comprising a calcium salt and salts of phytic acid, without or without zinc, or by continuing, less frequent phlebotomy.

31 Claims, 1 Drawing Sheet

OTHER PUBLICATIONS

Facchini, F., et al., "Relation Between Dietary Vitamin Intake and Resistance to Insulin–Mediated Glucose Disposal in Healthy Volunteers," *Am. J. Clin. Nutr.,* vol. 63, 1996, pp. 946–949.

Fernandez–Real, J., et al., "Serum Ferritin as a Component of the Insulin Resistance Syndrome," *Diabetes Care,* vol. 21, No. 1, Jan. 1998, pp. 62–68.

Finch, C.A. et al., "Effect of Blood Donation on Iron Stores as Evaluated by Serum Ferritin," *Blood,* vol. 50, 1977, pp. 441–447.

Ghidoni, A., et al., "Effect of Desferrioxamine Methansulphonate (DFOM) on Glucose Uptake by Rat Epididymal Adipose Tissue (30958)," *Proceedings of the Society for Experimental Biology and Medicine,* vol. 121, 1996, pp. 1039–1041.

Hallberg, L., et al., "Calcium: Effect of Different Amounts on Nonheme– and Heme–iron Absorption in Humans," *Am. J. Clin. Nutr.,* vol. 53, 1991, pp. 112–119.

Hallberg, L., et al., "Iron Absorption in Man: Ascorbic Acid and Dose–Dependent Inhibition by Phytate," *Am. J. Clin. Nutr.,* vol. 49, 1989, pp. 140–144.

Hunt, J.V., et al., "Oxidative Glycation and Free Radical Production: A Causal Mechanism of Diabetic Complications," *Free Rad. Res. Comms.,* vols. 12–13, 1991, pp. 115–123.

Jeppesen, J., et al., "Individuals with High Total Cholesterol/HDL Cholesterol Ratios are Insulin Resistant," *Journal of Internal Medicine,* vol. 243, 1998, pp. 293–298.

Lillioja, S., et al., "Insulin Resistance and Insulin Secretory Dysfunction as Precursors of Non–Insulin–Dependent Diabetes Mellitus," *The New England Journal of Medicine,* vol. 329, No. 27, pp. 1988–1992.

Lin, J., et al., "Convulsive Syncope in Blood Donors," *Annals of Neurology,* vol. 11, No. 5, May 1982, pp. 525–528.

Matthews, A.J., et al., "Iron and Atherosclerosis: Inhibition by the Iron Chelator Deferiprone," *Journal of Surgical Research,* vol. 79, No. 1, Nov. 1997, pp. 35–40.

Meyers, D.G., et al., "Possible Association of a Reduction in Cardiovascular Events with Blood Donation," *Hematology,* 1978, pp. 188–193.

Nitenberg, A., et al., "Coronary Artery Responses to Cold Pressor Test and Flow Velocity Increase is Improved by Desferrioxamine but Not L–Arginine in Diabetic Patients," *Archives Des Maladies Du Coeur et Des Vaisseaux,* vol. 90, No. 8, 1997, pp. 1037–1041.

Olefsky, J.M., et al., "Reappraisal of the Role of Insulin in Hypertriglyceridemia," *The American Journal of Medicine,* vol. 57, Oct. 1974, pp. 551–560.

Paolisso, G., et al., "Pharmacologic Doses of Vitamin E Improve Insulin Action in Healthy Subjects and Non–Insulin–Dependent Diabetic Patients," *Am. J. Clin. Nutr.,* vol. 57, 1993, pp. 650–656.

Pieper, G.M., et al., "Diabetes–Induced Endothelial Dysfunction is Prevented by Long–Term Treatment with the Modified Iron Chelator, Hydroxyethyl Starch Conjugated–Deferoxamine," *Journal of Cardiovascular Pharmacology,* vol. 30, 1997, pp. 734–737.

Potashnik, R., et al., "Regulation of Glucose Transport and GLUT–1 Expression by Iron Chelators in Muscle Cells in Culture," *The American Physiological Society,* 1995, pp. E1052–E1058.

Reaven, G.M., "Pathophysiology of Insulin Resistance in Human Disease," *Physiological Reviews,* vol. 75, No. 3, Jul. 1995, pp. 473–486.

Reaven, G.M., "Study of the Relationship Between Glucose and Insulin Responses to an Oral Glucose Load in Man," *Diabetes,* vol. 17, No. 9, Sep. 1968, pp. 560–569.

Reaven, G.M., et al., "Hypertension and Associated Metabolic Abnormalities—The Role of Insulin Resistance and the Sympathoadrenal System," *The New England Journal of Medicine,* vol. 334, No. 6, Feb. 8, 1996, pp. 374–381.

Reddy, M.B., et al., "The Influence of Different Protein Sources on Phytate Inhibition of Nonheme–Iron Absorption in Humans," *Am. J. Clin. Nutr.,* vol. 63, 1996, pp. 203–207.

Redmon, J.B., et al., "No Effect of Deferoxamine Therapy on Glucose Homeostasis and Insulin Secretion in Individuals With NIDDM and Elevated Serum Ferritin," *Diabetes,* vol. 42, Apr. 1993, pp. 544–549.

Spencer, C.M., et al, "Troglitazone," *Drugs,* vol. 54, No. 1, Jul. 1997, pp. 89–101.

Thompson, L.U., "Phytic Acid and Calcium Affect the In Vitro Rate of Navy Bean Starch Digestion and Blood Glucose Response in Humans," *Am. J. Clin. Nutr.,* vol. 46, 1987, pp. 467–473.

Tuomainen, T., et al., "Body Iron Stores Are Associated With Serum Insulin and Blood Glucose Concentrations," *Diabetes Care,* vol. 20, No. 3, Mar. 1997, pp. 426–428.

Yadrick, M.K., et al., "Iron, Copper, and Zinc Status: Response to Supplementation with Zinc or Zinc and Iron in Adult Females," *Am. J. Clin. Nutr.,* vol. 49, 1989, pp. 145–149.

Yoshioka, T., et al., "Studies on Hindered Phenols and Analogues. 1. Hypolipidemic and Hypoglycemic Agents with Ability to Inhibit Lipid Peroxidation," *J. Med. Chem.,* vol. 32, 1989, pp. 421–428.

Weintraub, L.R., "The Treatment of Hemochromatosis by Phlebotomy," *Med. Clin. North Am.,* vol. 50, No. 6, 1966, pp. 1579–1590.

"Deferoxamine Mesylate: Heavy Metal Antagonists," *AHFS Drug Information,* 95, pp. 2080–2081, 1995.

"Report of the Expert Committee on the Diagnosis and Classification of Diabetes Mellitus," *Diabetes Care,* vol. 20, No. 7, Jul. 1997, pp. 1183–1197.

METHODS AND COMPOSITIONS FOR CONTROLLING IRON STORES TO TREAT AND CURE DISEASE STATES

FIELD OF THE INVENTION

The present invention relates generally to methods and compounds for controlling body iron stores to cure or mitigate the effects of disease states affected by iron metabolism. More specifically, the present invention relates to methods and compounds for reducing body iron stores to near iron deficiency to ameliorate and/or cure type II diabetes mellitus, primary hypertension and atherosclerosis.

BACKGROUND OF THE INVENTION

Much effort has been expended to find effective treatments and a cure to non-insulin dependent diabetes mellitus (NIDDM), also referred to as type II diabetes mellitus. In NIDDM, the body continues to produce insulin, however, the insulin is not as effective as it should be and glucose uptake by the muscles is inhibited (i.e., the body becomes resistant to the effect of insulin). Typically, NIDDM is controlled by diet, oral medication and eventually, by regular periodic insulin injection. In addition, because NIDDM generally has a long latent period in which the patient is asymptomatic, such patients are often afflicted by other disease states as a consequence of undetected NIDDM, such as atherosclerosis, by the time that the NIDDM symptoms become manifest.

Regular periodic insulin injections, while hailed as a breakthrough forty years ago, often adversely affect a diabetic patient's lifestyle and do not seem to prevent vascular complications. Accordingly, the search for less intrusive treatments has been ongoing. One area of research, for example, has been to reduce or delay glucose uptake within the small intestine, so as to moderate blood glucose levels. For example, Thompson et al., "Phytic acid and calcium affect the in vitro rate of navy bean starch digestion and blood glucose response in humans," Am. J. Clin. Nutr., 46:467–73 (1987), suggests that the addition of phytic acid to foods may be used to delay starch digestion and glycemic response, whereas the addition of calcium has an opposite effect. U.S. Pat. No. 4,952,568 to Sawai et al. is directed to methods for treating type II diabetes by administering phytic acid salts in amounts sufficient to moderate blood glucose levels. No effective clinical applications appear to have been developed from the foregoing research.

More recently, a number of studies have suggested an association between iron metabolism disorders, such as thalassemia and hemochromatosis, and a number of disease states, such as type II (non-insulin dependent) diabetes mellitus and atherosclerosis. For example, Matthews, et al., "Iron and Atherosclerosis: Inhibition by the Iron Chelator Deferiprone," J. of Surg. Res., 73:35–40 (1997) suggests that the iron chelator Deferiprone may be useful in reducing atherogenesis by serving as anti-oxidant, although the in-vivo results reported there were not statistically significant. Tuomainen et al., "Body Iron Stores Are Associated With Serum Insulin and Blood Glucose Concentrations," Diabetes Care, 20(3):426–428 (1997), conclude that mildly elevated body iron stores are associated with statistically significant elevations in glucose homeostasis.

In accordance with previously known methods, iron metabolism disorders, such as thalassemia or hemochromatosis have been treated using iron chelation therapy, typically using either Deferoxamine administered by timed intramuscular injection via a pump. More recently, the oral iron chelator Deferiprone has become clinically available, although such orally administered chelators do not appear to have the efficacy of injected drugs. Both of these drugs present toxicity issues that are outweighed only by their effectiveness in reducing body-iron stores. Neither drug is suitable for widespread use in patients not exhibiting effects of a serious iron metabolism disorder.

In view of the foregoing, it would be desirable to provide methods and compounds for lowering and controlling body iron stores to treat or cure disease states, such as NIDDM, certain types of primary hypertension, and atherosclerosis that may be significantly worsened by an otherwise normal amount of body iron.

It further would be desirable to provide methods and compounds for reducing iron absorption that have low toxicity and therefore may be used in large patient populations with little adverse impact.

It also would be desirable to provide methods and compounds that lower the risk of atherogenesis, and other disease states associated with high oxidative stress.

It still further would be desirable to provide methods and compounds for reducing and controlling iron body stores in a phased manner, wherein initial body iron stores are lowered to a desired level, and thereafter maintained at the desired level by reducing intestinal iron absorption using low-toxicity compounds.

SUMMARY OF THE INVENTION

In view of the foregoing, it is an object of the present invention to provide methods and compounds for lowering and controlling body iron stores to treat or cure disease states that may be worsened by an otherwise normal or high iron body stores, such as NIDDM.

It is another object of this invention to provide methods and compounds for reducing iron absorption that have low toxicity and therefore may be used in large patient populations with little adverse impact.

It is a further object of the present invention to provide methods and compounds that lower the risk of atherogenesis, certain types of primary hypertension, and other disease states associated with high oxidative stress.

It is a still further object of the invention to provide methods and compounds for reducing and controlling iron body stores in a phased manner, wherein initial body iron stores are lowered to a desired level, and thereafter maintained at the desired level by reducing intestinal iron absorption using low-toxicity compounds.

These and other objects of the invention are accomplished by providing methods and compounds that enable a phased reduction of body iron stores to a near iron deficiency level, and thereafter maintain the body iron stores at that level by reducing iron absorption from food. In the context of the present invention, near-iron deficiency is defined as a state of mild or borderline iron deficiency (e.g., serum ferritin levels less than about 40 ng/ml and transferrin iron saturation index (iron sat.) of 15% or less) without iron-deficiency induced anemia, or with a very mild degree of iron-deficiency induced anemia.

In a first phase of the method, a patient's body iron stores are reduced to a level of near iron deficiency by regular periodic phlebotomy or use of pharmacological agents, such as iron chelators, for example, over a period of six to twelve months. In a second phase, ingested iron absorption is controlled using an oral dose, taken at mealtimes, of an oral binding compound comprising a calcium salt and salts of phytic acid, zinc, metallporphyrins or soy-protein isolates, or by continuing, less frequent phlebotomy.

In accordance with the present invention, regular periodic phlebotomy of 500 cc is expected to remove about 200 to 250 mg of iron. With phlebotomies spaced at one-week to eight-week intervals, near iron deficiency levels, as reflected, for example, by serum ferritin levels preferably less than about 40 ng/ml, may be achieved in 6 to 12 sessions. During this intensive phase, oral folic acid or recombinant human erythropoietin may be provided to sustain and stimulate red blood cell production by the bone marrow and to reduce the risk of anemia. Alternatively, iron chelators, such as Deferiprone, may be used to rapidly reduce iron stores to a level at which fewer phlebotomy sessions are required to achieve near-iron deficiency.

In the second phase of treatment, ingested iron absorption is reduced to about 1–2 mg/day by having the patient ingest an oral dose, e.g., tablet or syrup, of an oral iron binding compound, preferably comprising a combination of phytic acid salts, such as sodium phytate, and a calcium salt, such as calcium carbonate, with or without zinc. Other pharmacological agents, such as metalloporphyrins or soy-protein isolates, may be used alone or in combination with the foregoing compounds to further control iron absorption.

In initial small-scale clinical trials conducted using the foregoing methods of the present invention, patients initially suffering from NIDDM exhibited glucose tolerance within normal ranges for fasting blood sugar tests after a first phase of treatment. In addition, the patients exhibited overall improvement in all risk factors for cardiovascular disease, including lower blood pressure and pulse, and a significant decrease in the ratio of total cholesterol to high density liproprotein cholesterol.

Methods of employing the compounds of the present invention to reduce absorption of ingested iron to treat hemochromatosis and the iron overload of thalassemia (due to repeated transfusions) are also provided. It is expected that the use of the second phase compounds in accordance with the principles of the present invention may reduce the frequency of phlebotomy or dosage of iron chelators used to treat those diseases, thereby improving such patient's quality of life.

BRIEF DESCRIPTION OF THE DRAWING

Further features of the invention, its nature and various advantages will be more apparent from the accompanying drawing and the following detailed description of the preferred embodiments, wherein.

DETAILED DESCRIPTION OF THE INVENTION

Figure 1:
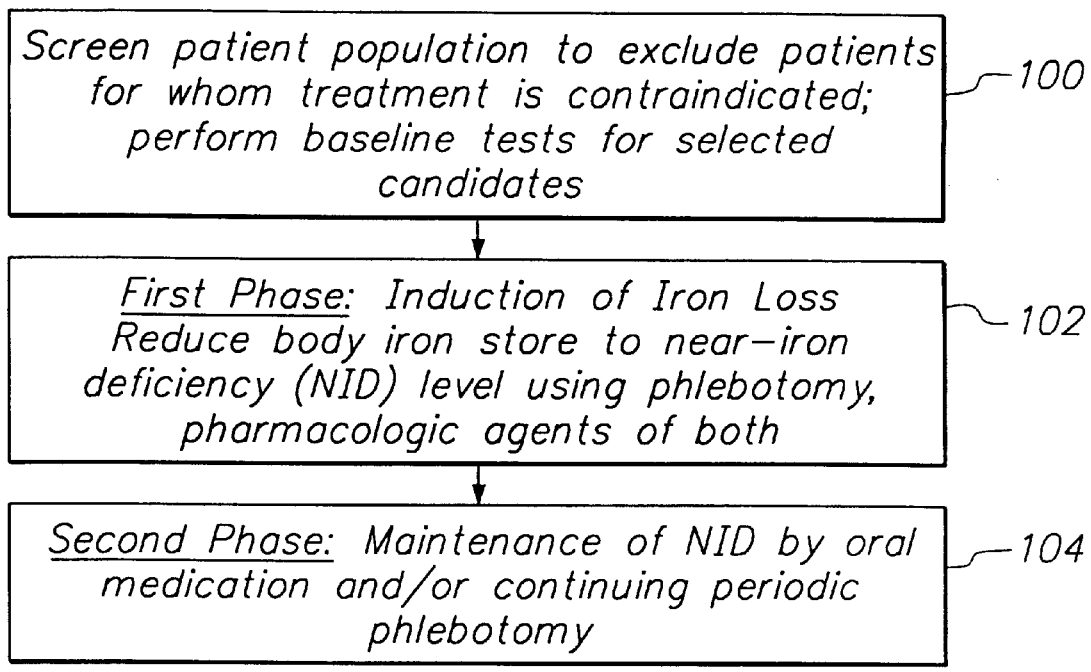
FIG. 1 is a flow chart of a method of the present invention for reducing and maintaining iron body stores to treat and/or cure disease states associated with normal to high iron body stores.

The present invention provides methods and compounds for treating and/or curing diseases associated with a relative or absolute increase of iron body stores, such as NIDDM, certain types of primary hypertension, and atherosclerosis.

An adult human male typically has a total body iron store of 2–4 gm, of which approximately 70% is incorporated in the circulating red blood cell mass. Applicant has discovered that induction of near-iron deficiency (NID), e.g., where serum ferritin levels are reduced to the range of about 40 ng/ml or less and the iron sat. to a level of 15% or less, has an insulin-sparing effect and reduces oxidative stress. Consequently, inducing and maintaining NID is expected to improve and/or cure NIDDM, reduce blood pressure, and lower other risk factors associated with cardiovascular disease. A mild degree of iron deficiency, without anemia or with a very mild degree of anemia, is not expected to cause any adverse side effects.

Treatment with the methods and compounds of the present invention is now described with respect to FIG. 1. The treatment of the present invention preferably involves a screening step, step 100, wherein suitable candidates are selected and unsuitable candidates for the treatment are excluded; a first phase, step 102, involving induction of the loss of body iron stores to a near-iron deficiency level; and a second phase, step 104, wherein body iron stores are maintained at NID.

Candidate Screening

In step 100 of the flow chart of FIG. 1, patients are first screened to select those candidates where application of the methods of the present invention is clinically indicated and where improvement is expected when treated in accordance with the principles of the present invention. This screening step also is intended to exclude those patients for whom the methods of the present invention are not indicated or may pose a risk. Subjects with NIDDM, primary hypertension and/or dyslipidemia, as indicated, for example, by a total cholesterol/HDL ratio of 5 or greater are a primary target population for treatment in accordance with the present invention. Preventative treatment in asymptomatic siblings and offspring of patients with NIDDM and primary hypertension also may be considered, particularly if the ratio TC/HDL is 5 or higher.

Patients exhibiting any of the following abnormalities should generally be excluded: (a) anemia; (b) hemodynamically significant coronary atherosclerosis (CAD), with or without symptoms; (c) coexistence of NIDDM with diseases such as cancer, renal or liver failure and other diseases that can cause secondary Diabetes, such as chronic pancreatitis, Cushing's Syndrome or pheochromocytoma; (d) grade 3 or 4 heart failure; and (e) pregnancy. While conditions (a) to (d) generally contraindicate undertaking the first phase of treatment, described hereinbelow, exceptions may be made on individual cases, based on the clinician's assessment of a specific patient's health. In addition, patients with a history of stroke or cerebrovascular or coronary artery disease generally should be excluded, although exceptions may be made for very stable patients, again based on clinical judgment.

Patients selected as candidates for treatment generally should undergo the following screening tests, which will enable the clinician to monitor the patients' health and quantify the impact of the treatment: (a) a complete physical exam; (b) routine blood chemistry testing; (c) blood count with differential (CBC); and (d) analysis of serum iron, ferritin and transferrin (TIBC) levels; and (e) urinalysis. For patients over the age of 50, or for smokers of any age, an exercise tolerance test (ETT) using 12 lead electrocardiography may be desirable as a diagnostic tool to detect asymptomatic coronary artery disease of hemodynamic significance.

First Phase: Induction of Iron Loss

Referring now to step 102 of FIG. 1, a first phase of treatment in accordance with the principles of the present invention is described. In particular, once the patients pass screening step 100, regular and periodic phlebotomy is undertaken, for example, every 1 to 8 weeks, until iron stores are lowered to near iron deficiency (NID), e.g., as indicated by serum ferritin levels below about 40 ng/ml or less and a level of iron sat. of 15% of less. With each phlebotomy, about 500 cc of blood is withdrawn from an antecubital superficial vein, and is expected to result in the removal of about 200 to 250 mg of iron per session.

Phlebotomy is safe and effective treatment for lowering iron body stores, and has been utilized for decades to treat patients afflicted with genetic hemochromatosis, as described, for example, in Dymock et al., "Observations on the pathogenesis, complications and treatment of diabetes in 115 cases of hemochromatosis," *Am. J. Med.*, 52:203–207 (1972) and Weintraub et al., "The Treatment of Hemochromatosis by Phlebotomy," *Med. Clin. North Am.*, 50(6):1579–1590 (1966).

During the first phase of treatment, represented by step 102, patients preferably are supplemented with oral folic acid, e.g., at a dosage of 1 mg per day, to sustain the increased red blood cell production rate by the bone marrow and prevent anemia. Alternatively, or in addition, regular periodic injections of recombinant human erythropoietin may be administered to stimulate production of red blood cells in the bone marrow, thus enabling phlebotomies to be performed more frequently. The use of such injections is described, for example, in Inoue et al., "Recovery of pancreatic beta-cell function in hemochromatosis: combined treatment with recombinant human erythropoietin and phlebotomy," *Am. J. Med. Sci.*, 314(6):401–402 (1997).

Throughout the first phase of treatment, which generally is expected to take from 4 to 18 months, serum ferritin, TIBC and serum iron concentrations are periodically monitored. Phlebotomies are discontinued when iron indexes show a state of low-normal to borderline iron deficiency without anemia or with very mild anemia, referred to herein as a state of near-iron deficiency (NID). If anemia ensues before NID is achieved, phlebotomies are suspended until CBC normalizes, as determined, for example, by weekly CBC testing.

Alternatively, the first phase of iron reduction may be achieved using a combination of pharmacological agents and phlebotomy. Continuous subcutaneous infusion of Deferoxamine, or more preferably, regular oral doses of Deferiprone, may be administered during the first phase as an alternative to, or in addition to, regular phlebotomy. Because such iron chelators are not expected to be capable of achieving near-iron deficiency, however, these pharmacological agents are viewed mostly as an adjunct to phlebotomy. Moreover, in view of the technical complexity of treatment and potential toxicity, ranging from cosmetic allergic reactions to death, use of such agents in a large patient population may not be preferred.

Phlebotomy is a safe procedure used by blood banks to collect blood and blood products. The only side effect to be expected is syncope, i.e., a fainting spell. This side effect is rare and usually may be prevented by performing the venipuncture and the phlebotomy in supine position, by checking the blood pressure afterwards and (in hypotensive subjects) by avoiding sudden orthostatic changes within the 30 minutes following phlebotomy. The ingestion of fluids and food during or immediately after the procedure typically mitigates any adverse reaction. Infrequently, infection and bruising may occur at the site of venipuncture, although these events are easily reversed by appropriate treatment.

Since a reduction of blood pressure may occur as a result of phlebotomy, hypertensive patients on medications should be warned of the symptoms of hypotension. In such cases, blood pressure medications should be suspended (especially before phlebotomy), tapered, or discontinued. For patients with diabetes, hypoglycemia awareness should be underlined and the necessary measures (e.g., diabetic medication tapering) implemented.

Patients with asymptomatic coronary or cerebral artery disease of hemodynamic relevance might, during phlebotomy (and because of the sudden 500 cc blood loss), experience hypotension. Either a heart attack or a stroke theoretically could be induced. In subjects at high risk for such events, screening with an ETT is advisable. If the ETT is negative but clinical suspicion still high, an infusion of 0.5 liter normal saline, simultaneous to phlebotomy, may prevent or reduce the degree of hypotension. Alternatively, smaller volume phlebotomies (250–400 cc) may be performed to induce less hypotension or for particularly small-framed individuals.

Second Phase: Maintaining NID

Referring now to step 104 of FIG. 1, a second phase of treatment in accordance with principles of the present invention is described. During this phase, target body iron stores are maintained at the NID level either by (a) reducing absorption of ingested iron, e.g., by taking oral medications with each meal or (b) by continuing phlebotomy.

A. Oral medications

Oral medications prepared in accordance with the present invention may be used to decrease intestinal iron absorption to achieve a daily iron balance near zero or very mildly positive. The daily iron balance is computed as that amount of iron absorbed from dietary intake minus the amount of iron lost by sweating and epidermal shedding from the gut and urinary tract. Typical daily iron loss is about 1 mg/day. The second phase of treatment therefore has a goal of reducing the absorption of ingested iron to about 1–2 mg/day.

Applicant has identified that several compounds may be used, alone or more preferably in combination, to reduce intestinal absorption of iron (IAI): calcium salts, myoinositol hexaphosphate (phytate and salts thereof), zinc, metalloporyhrins and soy-protein isolates.

Calcium salts: All calcium salts are expected to be effective in reducing IAI in a dose-dependent fashion and probably to a similar extent. For example, Hallberg et al., in "Calcium: effect of different amounts of on non-heme and heme iron absorption in humans," *Am. J. Clin. Nut.*, 53:112–119 (1991) report that calcium carbonate in doses of about 300 mg per meal decreases IAI from both heme and non-heme iron sources by about 50–60%. Above about 600 mg per dose, much higher doses are required for further, but much smaller, increments in IAI inhibition.

Phytate: Phytates form highly insoluble complexes with iron, significantly reducing IAI. As reported by Reddy et al., "The influence of different protein sources on phytate inhibition of non-heme iron absorption in humans," *Am. J. Clin. Nutr.*, 63:203–207 (1996) and Hallberg et al., "Iron absorption in man: ascorbic acid and dose-dependent inhibition by phytate," *Am. J. Clin. Nutr.*, 49:140–144 (1989), a dose of sodium phytate ranging between 50–300 mg, consumed at the time of a meal reduces IAI by about 85%.

Zinc: While the effect of zinc on human IAI has not been well studied, it is probable that zinc is less potent in humans than in rats, as reported in Yadrick et al., "Iron, copper and zinc status: response to supplementation with zinc or zinc and iron in adult females," *Am. J. Clin. Nutr.*, 49:145–150

(1989). However, those studies have shown that in fertile women, 50 mg of zinc/day administered over a 10 week period was effective in reducing serum ferritin levels by about 20%.

Metalloporyphrins: IAI also may be inhibited using orally ingested dosages of certain metalloporphyrins, such as tin protoporyphyrin, tin mesoporphyrin, chromium protoporyphyrin and chromium mesoporphyrin, as described in U.S. Pat. No. 5,223,494 to Kappas et al., which is incorporated herein by reference. In addition, it is expected that zinc protoporyphyrin and zinc mesoporphyrin also may be useful in inhibiting IAI.

Soy-protein isolates: Lynch et al. report in "Inhibitory effect of a soybean-protein-related moiety on iron absorption in humans," Am. J. Clin. Nutr. 60:567–572 (1994), that conglycinin, an isolate of soybean protein, may have utility in inhibiting IAI. Specifically, ingesting 30 gm of the conglycinin fraction of soy protein reduced IAI up to 50%.

In accordance with the present invention, compounds containing mixtures of calcium carbonate and salts of phytic acid, such as sodium phytate, with or without zinc, are prepared in an oral dosage form for ingestion at mealtimes. While calcium and phytate individually have been demonstrated to be effective at inhibiting IAI, it is expected that dosage forms comprising a combination of these compounds will be more powerful in decreasing IAI, for example, by inhibiting the absorption of both non-heme and heme iron.

Illustrative compounds prepared in accordance with the present invention may therefore comprise the following, which are provided for purposes of illustration, not limitation:

EXAMPLE 1

A tablet comprising 25–500 mg of a non-toxic salt of the phytic acid, such as sodium phytate or zinc phytate.

EXAMPLE 2

A capsule comprising 300–600 mg of a non-toxic calcium salt, such as calcium carbonate.

EXAMPLE 3

A tablet comprising from 10 to 80% by weight of a non-toxic salt of calcium and by 20 to 90% by weight of a non-toxic salt of phytic acid. Such mixtures are expected to be particularly beneficial because whereas the phytic acid is effective in binding with non-heme iron, calcium has been demonstrated to be effective in inhibiting IAI of both heme and non-heme iron.

EXAMPLE 4

A granulated powder comprising the composition of Example 3 plus from 5 to 10% by weight zinc.

EXAMPLE 5

A syrup comprising from 10 to 80% by weight of a non-toxic salt of calcium, such as calcium carbonate or calcium phosphate, 10 to 50% by weight of a non-toxic salt of phytic acid, such as sodium phytate, and a complimentary amount of zinc.

EXAMPLE 6

A liquid comprising the composition of either Example 3 or 4 further comprising an amount of a compound selected from the group consisting of tin protoporphyrin, tin mesoporphyrin, chromium protoporphyrin and chromium mesoporphyrin, zinc protoporphyrin and zinc mesoporphyrin.

EXAMPLE 7

A beverage comprising between 30–60 gm of the conglycinin fraction of soy protein.

The compositions of all of the foregoing examples are prepared in accordance with previously known pharmacological preparation techniques, which are per se known. In step 104 of FIG. 1, therefore, the patient preferably takes an oral dose, e.g., a 50–1000 mg tablet, with each meal, thereby reducing IAI to maintain the total body iron store near NID.

In addition, during step 104, the patient's diet preferably is monitored to avoid ingestion of compounds known to enhance intestinal absorption of iron, such as ascorbic and citric acid. For example, Hallberg et al., in "Iron absorption in man: ascorbic acid and dose-dependent inhibition by phytate," Am. J. Clin. Nutr., 49:140–144 (1989), report that ascorbic acid enhances IAI and offsets the inhibitory effect of phytate. Accordingly, the use of such compounds or of foods containing them in abundance (such as citrus juices and sodas) should be avoided, at least in concomitance with main meals or until digestion is completed.

Red meats also enhance IAI, in part because meats may contain substantial amounts of iron and in part because meats also enhance the absorption of iron contained in other foods. Thus, during the second phase of treatment, the patient's diet should include meats, and particularly red meats, sparingly. Similar considerations apply to iron-fortified foodstuffs.

In addition to use during the maintenance phase of treatment, step 104, the foregoing oral iron binders also may be used during the first phase of treatment. It is expected that establishing a less positive daily iron balance may result in fewer phlebotomies being needed to deplete iron stores.

Moreover, if the first phase of treatment (step 102) is administered slowly, over a period of years, the use of the foregoing oral iron binders alone may be reasonably efficient. If a negative iron balance can be induced (i.e., if IAI is reduced to <1 mg/day) for a sufficient length of time, then oral iron binders may be as effective as phlebotomy in depleting iron stores. For patients with body iron stores between 0.5 to 1 gram, NID could be achieved in 12–36 months. Accordingly, for patients with iron indexes indicating iron stores in the low range of normal, as well as in patients for whom the first phase of treatment is contraindicated due to a history of stroke or heart disease, oral iron binders may be a reasonably efficient alternative to phlebotomy.

The foregoing compounds also may be advantageously employed to reduce absorption of ingested iron to treat thalassemia and hemochromatosis. For example, administration of use of oral doses of mixtures of calcium salts and phytates, either with or without zinc, at mealtimes may beneficially inhibit intestinal iron absorption and may reduce the frequency of phlebotomy or dosage of iron chelators used to treat diseases, such as thalassemia and hemochromatosis, thereby improving such patients' quality of life.

B. Continuing Phlebotomy

During the second phase of treatment, target iron stores may be readily maintained by regular periodic phlebotomy, at less frequent intervals than in the first phase. Such intervals probably will be determined on individual basis, for example, averaging to about every 2–6 months, depending upon an individual patient's iron metabolism and diet.

Alternatively, treatment by oral medication, continued phlebotomy, or both, may be employed to induce and maintain near-iron deficiency. Depending upon the patient's initial body iron store, body size and average daily iron intake, an individualized treatment plan may be designed for each patient.

Preliminary Clinical Results

Six subjects achieved near iron deficiency, 2 with spontaneous blood loss (secondary to chronic peptic ulcer disease) and 4 with phlebotomies as described above with respect to step 102 of FIG. 1. No side effects were reported. Unless otherwise specified, results are expressed as mean ± standard error.

Mean age was 48±4 years, mean weight was 92±9 Kg, mean body mass index was 27.5±2.3 Kg/m$^2$, gender distribution was 5 males and one female. Mean duration of diabetes was 3.4±1.6 years. All but one patient were treated with either sulphonylureas or metformin. One patient was on dietary treatment only. Five patients were also on antihypertensive medications.

In all subjects, PCR and reverse dot blot genomic DNA analysis resulted negative for the two most common mutations detecting 85% of individuals with genetic hemochromatosis (GH). Further, none of the patients had a transferrin saturation index >50%. The chances of having missed GH in these patients were extremely low (perhaps 1:1000).

A sweat test questionnaire and a one-month dietary recall questionnaire were used to control for life-style changes that might confound study outcome interpretation. No changes in physical activity and in dietary recall were reported. Biochemical analysis was performed by previously known methods. Blood pressure and pulse rate were measured with an automatic monitor.

Near iron deficiency (NID) was achieved after an average of 9±3 phlebotomies. Serum ferritin concentration fell from 383±93 to 40±26 ng/mL and the transferrin iron saturation from 25±4 to 9±1% (p<0.001). The mean corpuscular cell volume (MCV) fell from 87±2 femtoliters (fl) to 82±2 (p<0.05). All subjects' Hgb and Hct were not significantly changed (i.e., no subject developed anemia) from baseline (14.5±5 to 14.1±0.7 g/dL; 42.6±0.9 to 42.0±1.8%, respectively; p=ns).

As a consequence of achieving NID, in two subjects, both antidiabetic and antihypertensive medications were discontinued. Table 1 shows the changes in weight, blood pressure and pulse rate; tables 2 and 3 show the changes in glucose and lipid profiles at baseline and after achieving NID. Significances were tested with 2-tail paired Student's t-test.

TABLE 1

Weight (in Kg), blood pressure (SBP = systolic blood pressure; DBP = diastolic blood pressure in mmHg) and pulse (rate/min) before and after achieving NID.

| variable | baseline | NID | p |
|---|---|---|---|
| weight | 92 ± 9 | 91 ± 9 | ns |
| SBP | 158 ± 10 | 149 ± 9 | ns |
| DBP | 88 ± 5 | 79 ± 4 | .08 |
| pulse | 75 ± 8 | 70 ± 5 | ns |

TABLE 2

Parameters of glucose control before (baseline) and after achieving near iron deficiency (NID). FBS = fasting blood sugar (mg/dL); fructosamine plasma concentration is in micromol/L.

| variable | baseline | NID | p |
|---|---|---|---|
| FBS | 178 ± 18 | 121 ± 11 | .03 |
| HgbAlc (%) | 8.2 ± .8 | 6.6 ± .5 | .009 |
| Fructosamine | 308 ± 39 | 233 ± 16 | .07 |

TABLE 3

Changes in lipid profile from baseline to near iron deficiency (NID). The change in triglyceride plasma concentrations trended towards significance. Lipid concentrations are expressed in mg/dL. TC/HDL = ratio between total and HDL cholesterol); HDL-c = high density lipoprotein cholesterol; LDL-c = low density lipoprotein cholesterol.

| variable | baseline | NID | p |
|---|---|---|---|
| TC/HDL | 6.6 ± 1.3 | 4.0 ± .6 | .01 |
| cholesterol | 214 ± 14 | 168 ± 20 | .02 |
| triglyceride | 241 ± 102 | 115 ± 38 | .07 |
| HDL-C | 36 ± 5 | 45 ± 3 | .05 |
| LDL-C | 134 ± 9 | 100 ± 19 | .01 |

With respect to the foregoing results, it is observed that baseline values of FBS would plainly lead to a diagnosis of NIDDM (mean FBS=178). After only the first phase of treatment, however, values of FBS were, on average, below the criteria for diabetes (mean FBS=121). Diabetes Mellitus here is diagnosed with FBS greater than 126 mg/dL, as promulgated by the American Diabetes Association, "Report of the Expert Committee on the Diagnosis and Classification of Diabetes Mellitus," *Diabetes Care,* 20(7):1183–1197 (1997). In addition, while some changes listed above were not statistically significant (such as changes in blood pressure), because the changes were observed using less medication, they are clinically significant.

Of equal importance, however, is that the foregoing results demonstrate a parallel improvement in all risk factors for cardiovascular disease: all the parameters measured (blood pressure, pulse rate, fasting blood glucose, glycosilated hemoglobin, cholesterols and triglycerides) are predictors of cardiovascular disease and death. While previously known methods exist for improving blood pressure, cholesterol or blood glucose, no previously known treatment (other than weight loss) has been shown to be effective in improving all major cardiovascular risk factors at once.

The foregoing results suggest that lowering body iron stores acts on a fundamental mechanism in the pathogenesis of NIDDM, high blood pressure and cardiovascular disease, conditions that present a high degree of clustering within the same individuals.

Observations on Iron Metabolism

The precise molecular mechanism of how lowering body iron stores to a level of near iron deficiency improves blood pressure, glucose tolerance and blood lipid concentration towards a less atherogenic pattern is unknown. Applicant theorizes, based on the foregoing results, and predecessor studies in patients with NIDDM, that two mechanisms may be postulated: (1) near-iron deficiency has an insulin-sparing effect; and (2) near-iron deficiency reduces oxidative stress. These theories, which should not be understood as limitations on the beneficial nature of the above-described methods and compounds or otherwise binding, are set forth below:

(1) NID has an insulin-sparing effect

An abnormally high blood glucose level is a universal finding in NIDDM. For three decades, it has been recognized that in the early stages of NIDDM, both glucose and insulin levels are high, indicating resistance to insulin-stimulated whole body glucose uptake. See, e.g., Reaven et al., "Plasma insulin response to an oral glucose load in humans," *Diabetes,* 17:560–569 (1968). Thus, if a patient is insulin resistant, the average day-long blood insulin level will be progressively higher, corresponding to the degree of insulin resistance.

There is consensus within the medical community that insulin resistance (and high insulin levels) are present well before the onset of the symptoms of NIDDM (i.e., before blood glucose levels become abnormally elevated). This in turn suggests that insulin resistance and higher than normal blood insulin levels may be a cause of NIDDM, rather than an effect. In this context, NIDDM is seen as the result of a failure of the insulin-producing cells to keep up with such a high production rate of insulin. If this were true, an intervention that would reduce the amount of insulin needed to maintain normal blood glucose levels might be effective in either preventing or curing the disease.

Near-iron deficiency and iron deficiency have been shown to enhance insulin-independent skeletal muscle glucose uptake, at least in vitro, as reported in Potashnik et al., "Regulation of glucose transport and glut-1 expression by iron-chelators in muscle cells in culture," *Am. J. Physiol.,* 269:E1052–E1058 (1995). Applicant's own studies have shown that lowering body iron stores decreases blood pressure, glucose and insulin levels in healthy volunteers and as shown in Preliminary Clinical Results discussed above, serum glucose, triglyceride (TG) and TC/HDL (a marker of insulin resistance) in patients with diabetes.

As reported in Olefsky et al., "Reappraisal of the role of insulin in hypertriglyceridemia," *Am. J. Med.,* 57:551–560 (1974) and Reaven et al., "Hypertension and associated metabolic abnormalities—the role of insulin resistance and the sympathoadrenal system," *New Eng. J. Med.,* 334:374–381 (1996), elevated insulin levels are suspected to increase TG, TC/HDL and water and salt retention (and therefore blood pressure). It is thus reasonable to suppose that near-iron deficiency counteracts these effects by correcting (or at least ameliorating) one of the fundamental defects shared by individuals with NIDDM, high blood pressure and atherosclerosis: elevated insulin levels.

As early as 1966, Ghidoni et al., in "Effect of desferal on glucose uptake by rat epididymal adipose tissue," *Proc. Soc. Exp. Biol.,* 121:1039–1040 (1966), reported that iron chelation enhances glucose transport at the level of tissue cultures of fat cells. Twenty years later, Potashnik et al., in "Regulation of glucose transport and glut-1 expression by iron-chelators in muscle cells in culture," *Am. J. Physiol.,* 269:E1052–E1058 (1995), reported a similar effect in rat skeletal muscle.

Results to date on human subjects have been inconclusive, however. Cutler, in "Deferoxamine therapy in high ferritin diabetes," *Diabetes,* 38:1207–1210 (1989), reported that treatment with the iron chelator deferoxamine improved diabetic control and allowed 10 subjects to discontinue insulin treatment. These findings were not validated, however, by Redmon et al., "No effect of deferoxamine therapy on glucose homeostasis and insulin secretion in individuals with NIDDM and elevated serum ferritin," Diabetes, 42:544–549 (1993), who found no effect of Deferoxamine on glucose control in 10 diabetics treated with an identical protocol. This discordance may be due to patient selection bias and to the inability of chelators to sufficiently lower iron body stores.

(2) NID lowers oxidative stress

Reported experimental data increasingly favors the hypothesis that in NIDDM excessive oxidative stress exists and may play a major role in the pathogenesis of associated vascular complications. Oxidative cell damage appears to be proportional to free and ferritin-bound iron concentration. For example, Balla et al., in "Hemin: a physiological mediator of low density lipoprotein oxidation and endothelial injury," *Arterioscler. Thromb.,* 11:1700–1711 (1991) reports that free hydroxyl radical production is enhanced by iron with consequent oxidative damage to enzymatic and structural proteins of endothelial and subendothelial cell membranes, causing endothelial dysfunction, LDL subendothelial accumulation and oxidation and consequent atherogenesis. See also, e.g., Matthews et al., "Iron and Atherosclerosis: Inhibition by the Iron Chelator Deferiprone," *J. Surg. Res.,* 73:35–40 (1997).

It has observed by Nitenberg et al., in "Coronary artery responses to cold pressor test and flow velocity increase is improved by deferoxamine in diabetic patients," *Arch. Mal Coeur,* 90:1037–1041 (1997) that the iron chelator deferoxamine improves the endothelial dysfunction present in NIDDM. Given the observation that the higher the serum ferritin and body iron stores, the higher the blood insulin level, as reported in Tuomainen et al., "Body Iron Stores Are Associated With Serum Insulin and Blood Glucose Concentrations," *Diabetes Care,* 20(3):426–428 (1997), it may be postulated that insulin resistance itself might be the result (or at least be worsened) by an imbalance between pro-oxidative and antioxidative forces at endothelial and subendothelial levels.

Support for such a theory comes not only from data linking insulin resistance to higher ferritin and iron stores, such as Fernandez-Real et al., "Serum Ferritin as a component of the insulin resistant syndrome," *Diabetes Care,* 21:62–68 (1998), but also from cross-sectional and prospective evidence demonstrating that individuals with a higher dietary intake of antioxidant compounds (vitamin A, E, oleuropeins and alcoholic beverages) are less insulin resistant, as reported in Facchini et al., "Light to moderate alcohol intake is associated with enhanced insulin sensitivity," *Diabetes Care,* 17:115–119 (1994), Facchini et al., "Relationship between dietary intake and resistance to insulin-mediated glucose disposal in healthy volunteers," *Am. J. Clin. Nutr.,* 63:946–959 (1996) and Paolisso et al., "Pharmacologic doses of vitamin E improve insulin action in healthy subjects and non insulin dependent diabetic patients,"*Am. J. Clin. Nutr.,* 57:650–656 (1993). Moreover, the novel antidiabetic agent Troglitazone, which has a weak insulin action-enhancing property, also inhibits LDL oxidation (29) and is, itself, a vitamin E analog, as described in Cominacini et al., "Troglitazone reduces LDL oxidation and lowers plasma E-selectin concentration in NIDDM patients," *Diabetes,* 47:130–133 (1998).

It is therefore expected that a diet rich in antioxidant compounds (vitamin A, E, oleuropeins, polyphenolic compounds, etc.), may have synergistic effects to iron lowering in the management of patients with NIDDM, primary hypertension and atherosclerosis.

What is claimed is:

1. A method of reducing and maintaining body iron stores of a patient to a near-iron deficiency level comprising:

during a first phase of treatment, reducing iron body stores to a near-iron deficiency level corresponding to a serum ferritin level less than about 40 ng/ml and an iron saturation index less than about 15%; and during a second phase of treatment, maintaining iron body stores at the near-iron deficiency level.

2. The method of claim 1 wherein, during the first phase, periodic phlebotomies are performed.

3. The method of claim 2 wherein, during the first period, the periodic phlebotomies are performed at regular intervals.

4. The method of claim 2 wherein, during the first phase, the patient ingests oral doses of an iron chelator.

5. The method of claim 2 wherein, during the first phase, an iron chelator is administered to the patient by continuous subcutaneous infusion.

6. The method of claim 1 wherein, during the second phase, periodic phlebotomies are performed.

7. The method of claim 1 wherein, during the second phase, the patient ingests an oral dose of an iron binding compound.

8. The method of claim 7 wherein the patient ingests the oral dose of the iron binding compound on a daily basis.

9. The method of claim 7 wherein, during the second phase, the patient ingests an oral dose of a compound selected from the group consisting of calcium salts, phytic acid salts, zinc, tin protoporphyrin, tin mesoporphyrin, chromium protoporphyrin and chromium mesoporphyrin, zinc protoporphyrin and zinc mesoporphyrin, conglycinin and mixtures thereof.

10. The method of claim 1 wherein the patient ingests the oral dose of the iron binding compound at mealtime.

11. A method of reducing and maintaining body iron stores of a patient to a near-iron deficiency level to alleviate symptoms of non-insulin dependent diabetes mellitus, primary hypertension and cardiovascular disease, the method comprising:

reducing body iron stores to a near-iron deficiency level corresponding to a serum ferritin level less than about 40 ng/ml and an iron saturation index less than about 15%; and administering to the patient an oral dose of an iron binding compound in an amount effective to inhibit intestinal iron absorption to maintain body iron stores at the near-iron deficiency level.

12. The method of claim 11 wherein reducing iron body stores comprises performing periodic phlebotomies.

13. The method of claim 12 wherein the periodic phlebotomies are performed at regular intervals.

14. The method of claim 12 wherein reducing iron body stores further comprises administering oral doses of an iron chelator.

15. The method of claim 12 wherein reducing iron body stores further comprises administering an iron chelator by continuous subcutaneous infusion.

16. The method of claim 11 wherein administering to the patient an oral dose of an iron binding compound comprises administering an oral dose of a compound selected from the group consisting of calcium salts, phytic acid salts, zinc, tin protoporphyrin, tin mesoporphyrin, chromium protoporphyrin, chromium mesoporphyrin, zinc protoporphyrin and zinc mesoporphyrin, conglycinin and mixtures thereof.

17. The method of claim 11 wherein the oral dose of an iron binding compound is administered daily.

18. The method of claim 11 wherein the oral dose of an iron binding compound is administered at mealtime.

19. A method of controlling body iron stores of a patient at a near-iron deficiency level comprising:

monitoring body iron stores by periodically testing the patient's blood to measure a serum ferritin level and an iron saturation level; and ingesting a sufficient oral dose of an iron binding compound on a daily basis to inhibit intestinal iron absorption and maintain body iron stores at a near-iron deficiency level corresponding to a serum ferritin level less than about 40 ng/ml and an iron saturation index less than about 15%.

20. The method of claim 19 further comprising performing phlebotomies on a periodic basis.

21. The method of claim 20 wherein the phlebotomies are performed at regular intervals.

22. The method of claim 20 wherein ingesting a sufficient oral dose of an iron binding compound comprises ingesting an oral dose of an iron binding compound at each mealtime.

23. The method of claim 20 wherein ingesting a sufficient oral dose of an iron binding compound comprises ingesting an oral dose of an iron binding compound selected from the group consisting of calcium salts, phytic acid salts, zinc, conglycinin and mixtures thereof.

24. The method of claim 20 wherein ingesting a sufficient oral dose of an iron binding compound comprises ingesting an oral dose of an iron binding compound selected from the group consisting of calcium salts, phytic acid salts, zinc, tin protoporphyrin, tin mesoporphyrin, chromium protoporphyrin and chromium mesoporphyrin, zinc protoporphyrin and zinc mesoporphyrin, conglycinin and mixtures thereof.

25. A method of controlling body iron stores of a patient at a near-iron deficiency level to alleviate symptoms of non-insulin dependent diabetes mellitus, primary hypertension and cardiovascular disease, the method comprising:

monitoring body iron stores by periodically testing the patient's blood to measure a serum ferritin level and an iron saturation level; and administering to the patient an oral dose of an iron binding compound in an amount effective to inhibit intestinal iron absorption and to reduce body iron stores to a near-iron deficiency level corresponding to a serum ferritin level less than about 40 ng/ml and an iron saturation index less than about 15%.

26. The method of claim 25 further comprising performing periodic phlebotomies.

27. The method of claim 23 wherein the periodic phlebotomies are performed at regular intervals.

28. The method of claim 25 wherein administering to the patient an oral dose of an iron binding compound comprises administering an oral dose of a compound selected from the group consisting of calcium salts, phytic acid salts, zinc, conglycinin and mixtures thereof.

29. The method of claim 25 wherein administering to the patient an oral dose of an iron binding compound comprises administering an oral dose of a compound selected from the group consisting of calcium salts, phytic acid salts, zinc, tin protoporphyrin, tin mesoporphyrin, chromium protoporphyrin, chromium mesoporphyrin, zinc protoporphyrin and zinc mesoporphyrin, conglycinin and mixtures thereof.

30. The method of claim 25 wherein the oral dose of an iron binding compound is administered daily.

31. The method of claim 25 wherein the oral dose of an iron binding compound is administered at mealtime.

* * * * *